United States Patent [19]
Kawasaki et al.

[11] Patent Number: 6,101,239
[45] Date of Patent: Aug. 8, 2000

[54] MEDICAL IMAGING APPARATUS

[75] Inventors: Shinji Kawasaki, Matsudo; Shigeyuki Ikeda, Kashiwa, both of Japan

[73] Assignee: Hitachi Medical Corporation, Toky, Japan

[21] Appl. No.: 09/066,990

[22] Filed: Apr. 23, 1998

[51] Int. Cl.[7] .................................................. G01N 23/04
[52] U.S. Cl. ............................................ 378/63; 324/307
[58] Field of Search .................... 378/63, 98.8; 600/410, 600/425, 411, 427; 324/307, 309, 318

[56] References Cited

U.S. PATENT DOCUMENTS

| | | | |
|---|---|---|---|
| 5,419,320 | 5/1995 | Kawaguchi et al. | 128/633 |
| 5,485,087 | 1/1996 | Morich et al. | 324/318 |
| 5,713,357 | 2/1998 | Meulenbrugge et al. | 128/653.2 |

*Primary Examiner*—David V. Bruce
*Assistant Examiner*—Michael J. Schwartz
*Attorney, Agent, or Firm*—Pennie & Edmonds LLP

[57] ABSTRACT

A medical imaging apparatus comprises magnetic resonance imaging means (30) for obtaining a MR tomogram of an object to be examined, X-ray radiographic means (11,12,13) for obtaining a radiographic image of the object and imaging control means for controlling overall timings of application of magnetic fields and acquisition of the nuclear magnetic resonance signals in the MRI means and timing of X-ray emission in the X-ray radiographic means. In the medical imaging apparatus, MR imaging is carried out in parallel with X-ray radiography by controlling the timing of X-ray emission to be noncoincident with both the timing of application of magnetic fields and the timing of acquisition of NMR signals to obtain X-ray images and MR images both having approximately the same time phase.

24 Claims, 8 Drawing Sheets

MEDICAL IMAGING APPARATUS

BACKGROUND OF THE INVENTION

The present invention relates to a medical imaging apparatus, particularly to a medical imaging apparatus capable of providing both an X-ray image and a magnetic resonance tomogram approximately at the same time.

Figure 8:
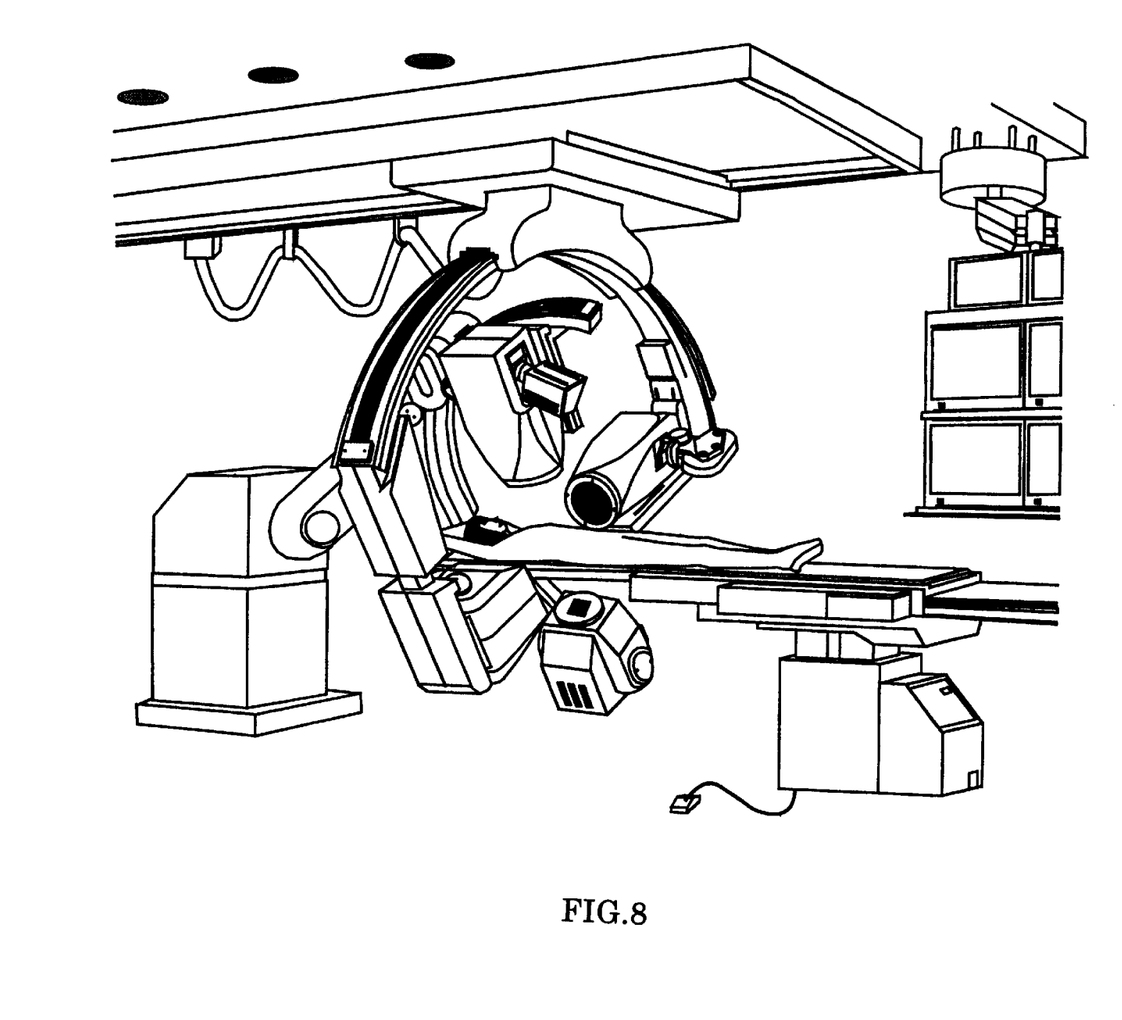
FIG. 8 is perspective view of a conventional X-ray radiographic apparatus of a bi-plane system.

Improved performance of diagnostic imaging apparatuses and of catheters and guiding wires has made available interventional radiology (referred to as IVR hereinafter), in which a catheter equipped with various instruments on its tip is inserted into a human body under X-ray fluoroscopy. This has enabled diagnosis and therapy of lesions to be conducted simultaneously. As a diagnostic apparatus for conducting IVR, an X-ray diagnosis apparatus of bi-plane system has been employed, which, as shown in FIG. 8, has two X ray tube and image intensifier (referred to as I.I. hereinafter) pairs supported face to face by a tube stand.

By using this X-ray diagnosis apparatus, images can be obtained from two directions simultaneously. However, these images can not provide three dimensional information regarding to the relationship between the tip of a catheter and a lesion since each of the images is a two dimensional fluoroscopic image. In addition, internal organs can not be observed in the two dimensional images because of their low X-ray absorptance. Therefore, it is hard to grasp the position of the catheter in regard to the organs.

On the other hand, an X-ray CT is known to be suitable for grasping the relative position of the organs and the catheter or the like. However, it can not be applied to the patient together with the X-ray diagnosis apparatus having a tube stand since the X-ray CT requires a scanner part which hampers the simultaneous application with the X-ray CT. Accordingly, when X-ray CT images are required during the application of X-ray fluoroscopy, the patient must be moved to the X-ray CT in order to take the CT image and confirm the relative position of the catheter and the organ. Then the patient has to be returned to the X-ray fluoroscopic apparatus to advance the catheter or collect tissue. However, it is dangerous and not desirable to move the patient with the catheter inserted.

There is another problem that the relative positions in the two images, i.e. the CT image and the fluoroscopic image, may be inconsistent since locomotion of the patient between the X-ray CT and the X-ray fluoroscopy takes at least several tens of seconds. For example, even though one apparatus is applied as the patient holds his breath, the same condition can not always be reproduced in the other apparatus. A slight time lag may produce change of the position of the organ and this change may make a precise diagnosis difficult.

SUMMARY OF THE INVENTION

An object of the present invention is to provide a medical imaging apparatus capable of providing both an X-ray image and a CT image including three dimensional position information approximately at the same time without moving the patient.

Another object of the present invention is, to utilize the fact that an open-gantry type magnetic resonance imaging apparatus (referred to as an MRI apparatus hereinafter) can be applied together with the X-ray radiographic apparatus structurally, to provide a method for obtaining both an X-ray image and an MRI image including three dimensional position information approximately at the same time.

The medical imaging apparatus of the present invention comprises magnetic resonance imaging means (referred to as MRI means hereinafter) for applying high frequency magnetic fields and gradient magnetic fields to an object (human body) placed in a static magnetic field according to a predetermined pulse sequence and obtaining a tomogram of the object based on nuclear magnetic resonance (NMR) signals emitted from the object, an X-ray radiographic means for obtaining a fluoroscopic (radiographic) image of the object and a means for controlling overall timing of application of magnetic fields and acquisition of NMR signals in the MRI means and timing of X-ray emission in the X-ray radiographic means. The control means preferably controls timing of operations of each means so that both the timing of application of magnetic fields and the timing of acquisition of NMR signals do not coincide with that of X-ray emission.

The X-ray radiographic means preferably employs a flat panel X-ray sensor as an X-ray detector.

In the medical imaging apparatus of the present invention, during operation of both the MRI means and X-ray radiographic means, the timing of application of magnetic fields and that of X-ray emission are controlled so that X-rays are emitted by the X-ray radiographic means only when neither frequency magnetic fields nor gradient magnetic fields are applied and no NMR signal is being detected. By this, the X-ray radiographic means can produce X-ray fluoroscopic images without interference from high frequency magnetic field of the MRI apparatus. At the same time, the MRI means can produce MRI images while avoiding the influence of electromagnetic noise of the X-ray radiographic means. Since the images obtained from the two means have almost the same time phase, diagnosis or therapy can be conducted efficiently by referring to these images.

The means for controlling the timing of application of magnetic fields and that of X-ray emission may be a controller superior to both the controller of the MRI means and that of the X-ray radiographic means or to only one of these controllers. In the latter case, the present invention is applicable without drastic changes in either the X-ray radiographic means or the MRI means. In addition, when the flat panel X-ray sensor is employed as an X-ray detector, X-ray images are not affected by the magnetic field even though magnetostatic shielding is not implemented.

In the medical imaging apparatus of the present invention, the MRI means and X-ray radiographic means are not always operated at the time as above-mentioned but they can be operated alternately or independently.

An imaging method using the medical imaging apparatus of the present invention preferably employs intermittent X-ray pulses as the X-rays emitted by the X-ray radiographic means. By using intermittent X-ray pulses, a time series of continuous X-ray images (dynamic images) can be obtained. In this method, by controlling both the timing of X-ray emission and that of magnetic field application by MRI, various kinds of imaging methods can be implemented.

In a preferred embodiment, X-rays are emitted at least one time within one cycle between applications of one high frequency magnetic field and the next. Such an X-ray pulse may be emitted between each pair of pulses constituting the pulse sequence or it may be emitted during the interval between consecutive cycles of the pulse sequence.

In another preferred embodiment, X-rays are emitted intermittently and continuously by the X-ray radiographic means and a pulse sequence for obtaining one MRI image is conducted during the interval between the X-ray emissions. For example, as a pulse sequence for obtaining a single image, echo planar imaging (EPI method) may be carried out during the interval between X-ray emissions.

The interval between X-ray emissions can be varied to the extent that it does not affect the dynamic images. In real time cine-imaging (radiography), X-ray pulses are emitted at relatively short intervals and the interval is often shorter than the period wherein the EPI sequence is performed. However, since the sequence is terminated within several 10 milliseconds, the interval between X-ray emission can be prolonged so as to insert the EPI sequence without any influence on the dynamic images.

DESCRIPTION OF THE PREFERRED EMBODIMENT

Preferred embodiments of the present invention will be explained in detail hereinafter.

Figure 1:
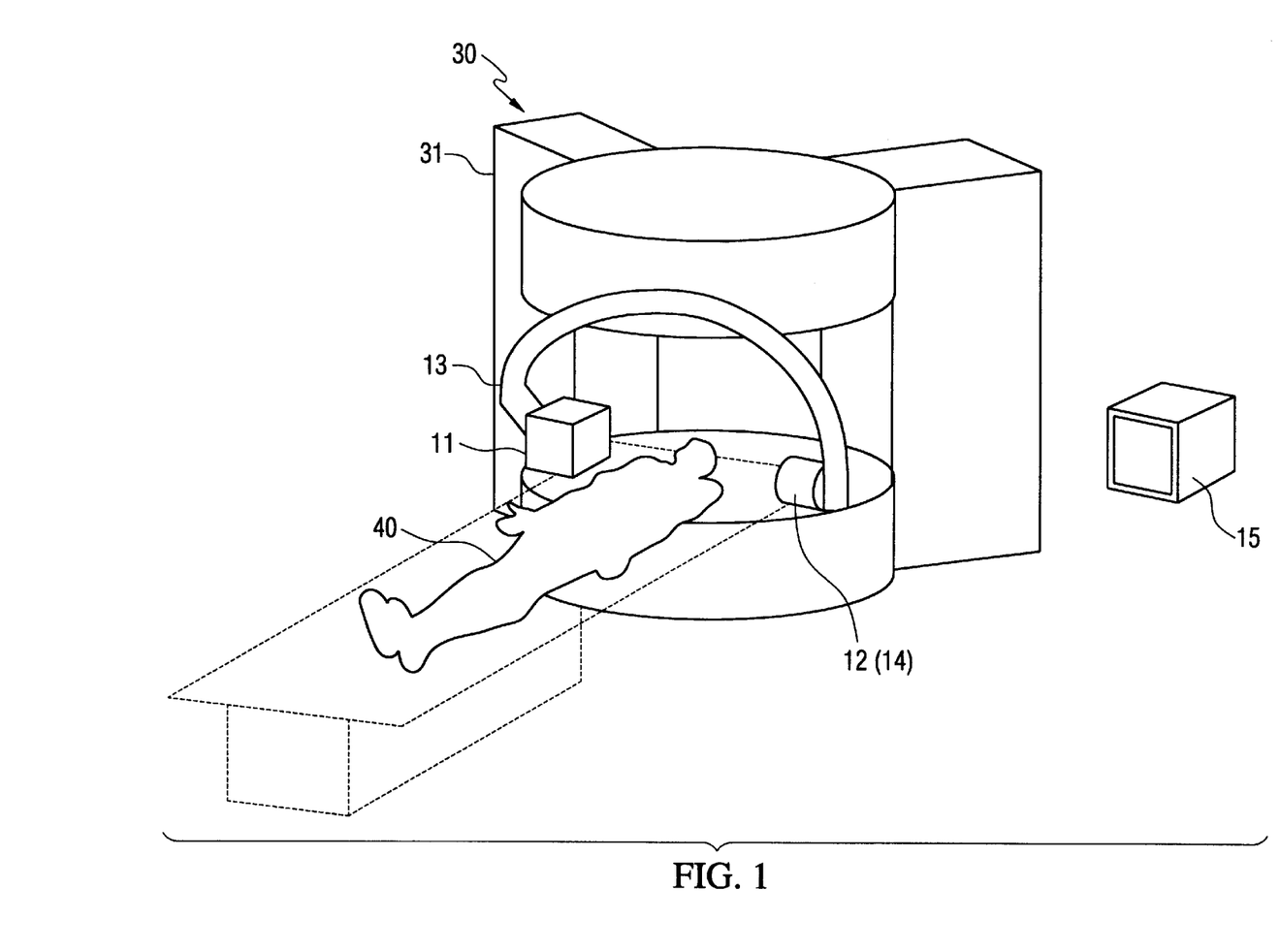
FIG. 1 is a perspective view of a preferred embodiment of a medical imaging apparatus according to the present invention.

The medical imaging apparatus of the present invention will be explained with reference of FIGS. 1 and 2. This medical imaging apparatus consists of an open-gantry type MRI apparatus (MRI means) 30, such as shown in FIG. 1, combined with an X-ray radiographic apparatus (X-ray radiographic means) 10 and a controlling means, not illustrated, which controls both the MRI apparatus 30 and the X-ray radiographic apparatus 10.

As illustrated, the X-ray radiographic apparatus 10 is provided with an X-ray tube 11, a flat panel X-ray sensor 12 using a solid detector, a C-shaped support 13 for holding them face to face, a TV camera 14 equipped with the flat panel X-ray sensor 12 and a monitor 15 for displaying images. In addition, as shown in FIG. 2, it is installed with a high voltage generator 16 which supplies a high voltage to the X-ray tube to generate X-rays, an X-ray controller 17 which outputs signals for generation of X-rays to the high voltage generator 16, an image processor 18 for processing acquired images and an operation panel (not illustrated) for inputting conditions (settings) to the X-ray controller 17.

Although the I.I. used in conventional X-ray radiographic apparatuses may be employed as an X-ray detector instead of the flat panel X-ray sensor, it must be provided with magnetic shielding. The flat panel X-ray sensor is preferable because it has a better X-ray detecting efficiency than the I.I. and thereby enables use of an X-ray tube of a smaller size than the conventional one as an X-ray source. Such a small X-ray source is adequate for X-ray fluoroscopy. Further, while the I.I. is sensitive to magnetic fields, the flat panel X-ray sensor is tolerant of the magnetic fields and does not need magnetic shielding.

As a flat panel X-ray sensor, any known X-ray detector can be employed. An X-ray detector consisting of Cesium Iodide (Cs I), a photo diode such as a silicon diode and TFT (thin film transistor) is exemplified. A combination of a photo diode and TFT may be amorphous silicon.

As shown in FIG. 1, the MRI apparatus 30 is the open gantry type. While the open gantry type MRI apparatus was developed to alleviate the oppressive feeling experienced by the patient, it is suitable for IVR since it provides the operator with free accessibility to the patient from any direction and, structurally, can be operated simultaneously with the X-ray apparatus 10. As a result, it is not necessary to move the patient in order to obtain images by both apparatuses.

Although not shown in the drawing, the gantry 30 is provided therein with a permanent magnet for generating a uniform static magnetic field, a high frequency coil for applying high frequency magnetic fields to excite protons in the object to be examined and a group of gradient magnetic field coils for adding necessary position information required for formation of images to NMR signals emitted from the object. In addition, a receiving coil is placed close to the operated part of the object.

As the receiving coil, an RF coil for a single use of receiver or an RF coil serving both as a receiver and a transmitter can be employed. When measurement of MRI and X-ray radiography are carried out at the same time, it must be placed so that an X-ray image of a conductor part, a metallic connector or a thick plastic part of the coil does not overlap an X-ray image of a portion of interest of the examined object. In order to avoid the overlap, the receiving coil is preferably placed so that at least above-mentioned parts of the coils does not intercept X-ray beams which transmit the portion of interest.

Figure 2:
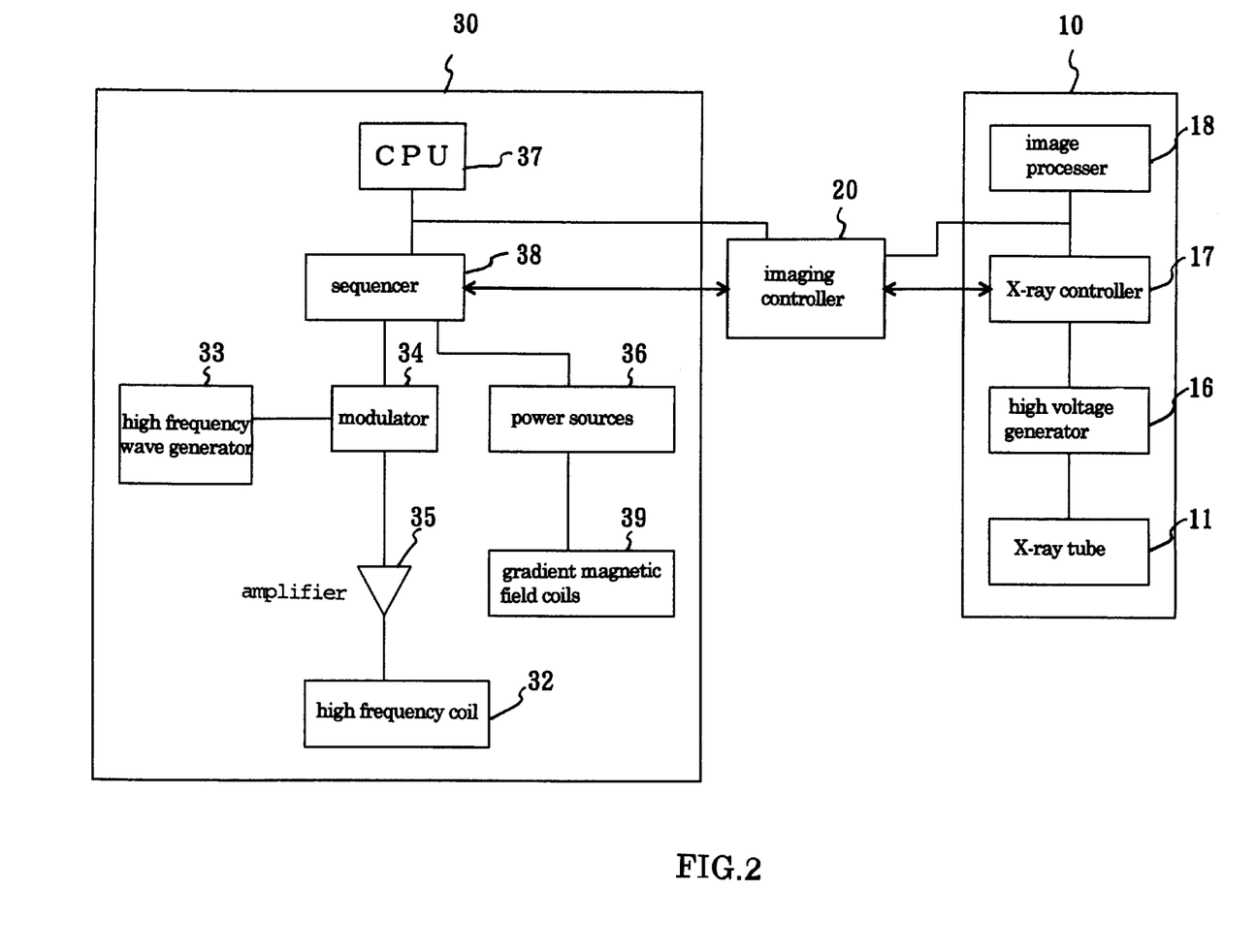
FIG. 2 is a block diagram showing the interconnection of components in the medical imaging apparatus of the present invention.

As shown in FIG. 2, the MRI means further comprises a high frequency wave generator 33 for applying high frequency magnetic field pulses, a modulator 34 for modulating the high frequency waves, an amplifier 35 for amplifying the modulated signals and outputting them to a transmission coil 32, and a power source 36 for supplying electric power to each of the gradient magnetic field coils to apply gradient magnetic fields. In addition, it has an MRI controller (CPU) 37 for controlling the whole apparatus, an operation panel (not shown) for inputting the various conditions and a sequencer 38 for producing series of pulse sequences under the control of the MRI controller 37. The modulator 34 and the power source 36 are respectively involved in application of high frequency magnetic fields and in application of gradient magnetic fields and they drive the transmission coil 32 and the gradient magnetic field coils 39 respectively under instruction from the sequencer 38. Although not shown in the drawing, further provided are an image processor for producing images by processing the collected echo signals (NMR signals) and a monitor for displaying the processed images.

The imaging apparatus of the present invention further comprises an imaging controller 20 for overall control of the timing of X-ray pulse emission and the timing of application of magnetic fields. The imaging controller 20 is connected to the X-ray controller 17 of the X-ray radiographic apparatus 10 and to the sequencer 38 of the MRI apparatus 30.

One mode of operation of the above-mentioned apparatus will be explained with reference to FIG. 2.

In order to obtain X-ray images, various parameters such as tube voltage, tube current and the like are set up in the X-ray controller 17 through the operation panel of the X-ray radiographic apparatus 10. The X-ray controller 17 drives the high voltage generator 16 based on the parameters so that the X-ray tube 11 radiates X-rays. The X-rays are transmitted through the object under examination to the flat panel X-ray sensor 12, which converts X-ray absorption or decay to optical information. The optical information is made into an image by the TV camera 14. The image is processed by the image processor 18 and then displayed on the monitor 15.

In order to obtain MRI images, various parameters such as repetition time TR, echo time TE and the like are set up in the MRI controller 37 through the operation panel of the MRI apparatus 30. The sequencer 38 produces a predetermined pulse sequence based on the parameters, where the high frequency magnetic fields and the gradient magnetic fields are applied by the high frequency coil 32 and the gradient magnetic field coils 39 respectively. The echo signals emitted from the object under examination by application of these magnetic fields are received by the receiving coil and transmitted to the image processor of CPU 37. MRI images are formed here by two dimensional or three dimensional Fourier transform and exhibited on the monitor.

As mentioned above, while the X-ray radiographic apparatus 10 and the MRI apparatus 30 are set up through the associated operation panels, the timings of operating both apparatuses are controlled by the imaging controller 20. That is, pulse signals for generating gradient magnetic fields, pulse signals for generating high frequency waves and signals instructing acquisition of echo signals are inputted to the imaging controller 20 from the sequencer 38 and the imaging controller 20 determines and sends timing signals for X-ray emission to the X-ray controller 17 so that the emission times do not overlap with the times of application of magnetic fields and the like. Or a timing signal indicating X-ray emission is inputted into the imaging controller 20 from the X-ray controller 17 and the imaging controller 20 determines and outputs timing signals for generating high frequency pulses and the like to the sequencer 38 so that the times do not overlap with the times of X-ray emission. Thus, the times of application of high frequency magnetic fields and of gradient magnetic fields and that of echo signal acquisition are controlled by the imaging controller 20 to be different from the times of X-ray emission. Thus X-ray radiography and MRI can be carried out at the same time and an X-ray image and an MRI image both having approximately the same time phase can be obtained.

Figure 3A:
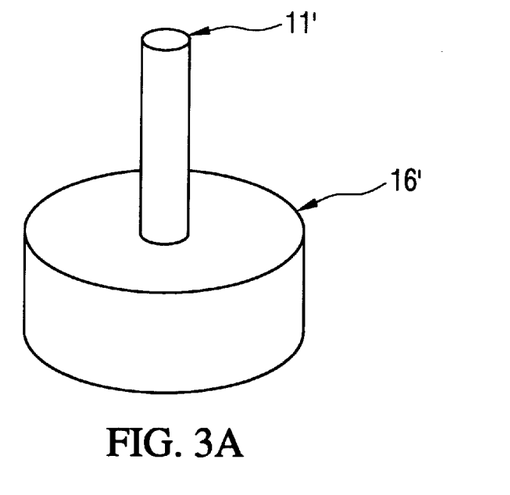
FIG. 3(a) is a perspective view showing a small-sized X-ray generator applied to the medical imaging apparatus of the present invention and (b) is a perspective view showing a medical imaging apparatus provided with the same.

Although an X-ray radiographic apparatus in which the X-ray tube 11 and the flat panel X-ray sensor 12 are supported by the support 13 with the C-shaped arm is exemplified in the embodiment shown in FIG. 1, when a small-sized X-ray generator is employed, this X-ray source and the flat panel X-ray sensor may be placed face to face within the gantry of the MRI apparatus since the flat panel X-ray sensor is thin. The small-sized X-ray generator which can be placed within the gantry may be the one shown in FIG. 3(a). This X-ray generator is provided with a high voltage generator 16' and accelerator 11' which is attached to the high voltage generator 16' and has a fixed target (not shown) for generating X-rays on its tip.

Figure 3B:
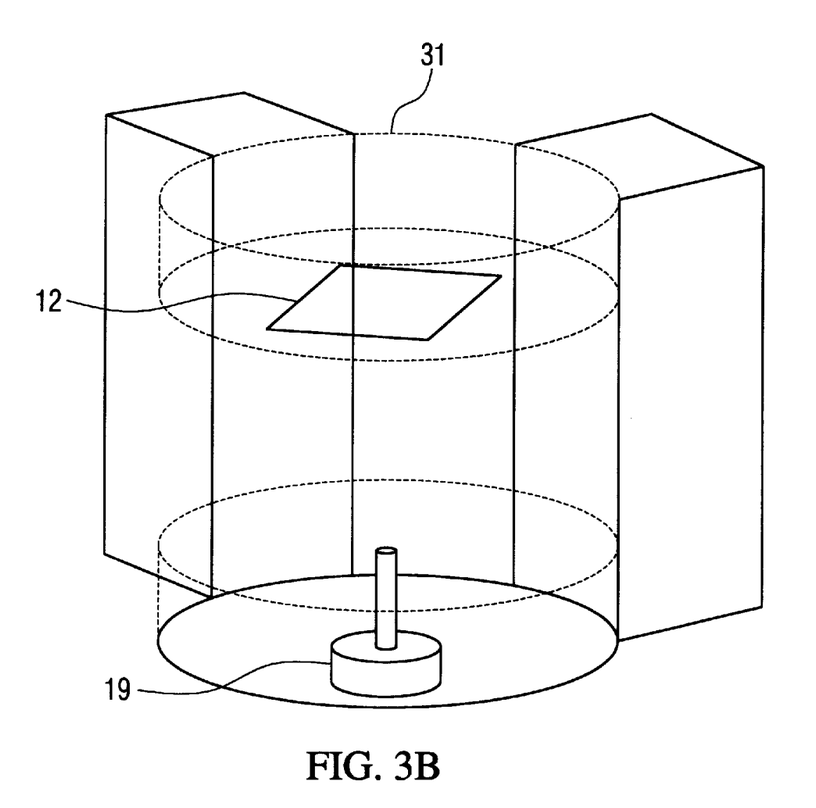

FIG. 3(b) shows the X-ray generator 19 and the flat panel X-ray sensor 12 which are placed within the gantry. In the figure, there is shown an open-gantry type MRI apparatus provided with a pair of magnet at the upper and lower sides between which a space for an object to be inserted is formed. The flatpanel X-raysensor 12 is positioned at the upper gantry part and the X-ray generator 19 is positioned at the lower gantry part. In this apparatus, X-ray is emitted from backside of the object lying in the space within the open gantry and transmitted through the object to the flat panel X-ray sensor 12. As previously mentioned, the receiving coil of the MRI apparatus should be placed so that the conductor or connector of the coil is positioned outside the path of X-ray beams which transmits a portion of interest of the object.

Figure 4:
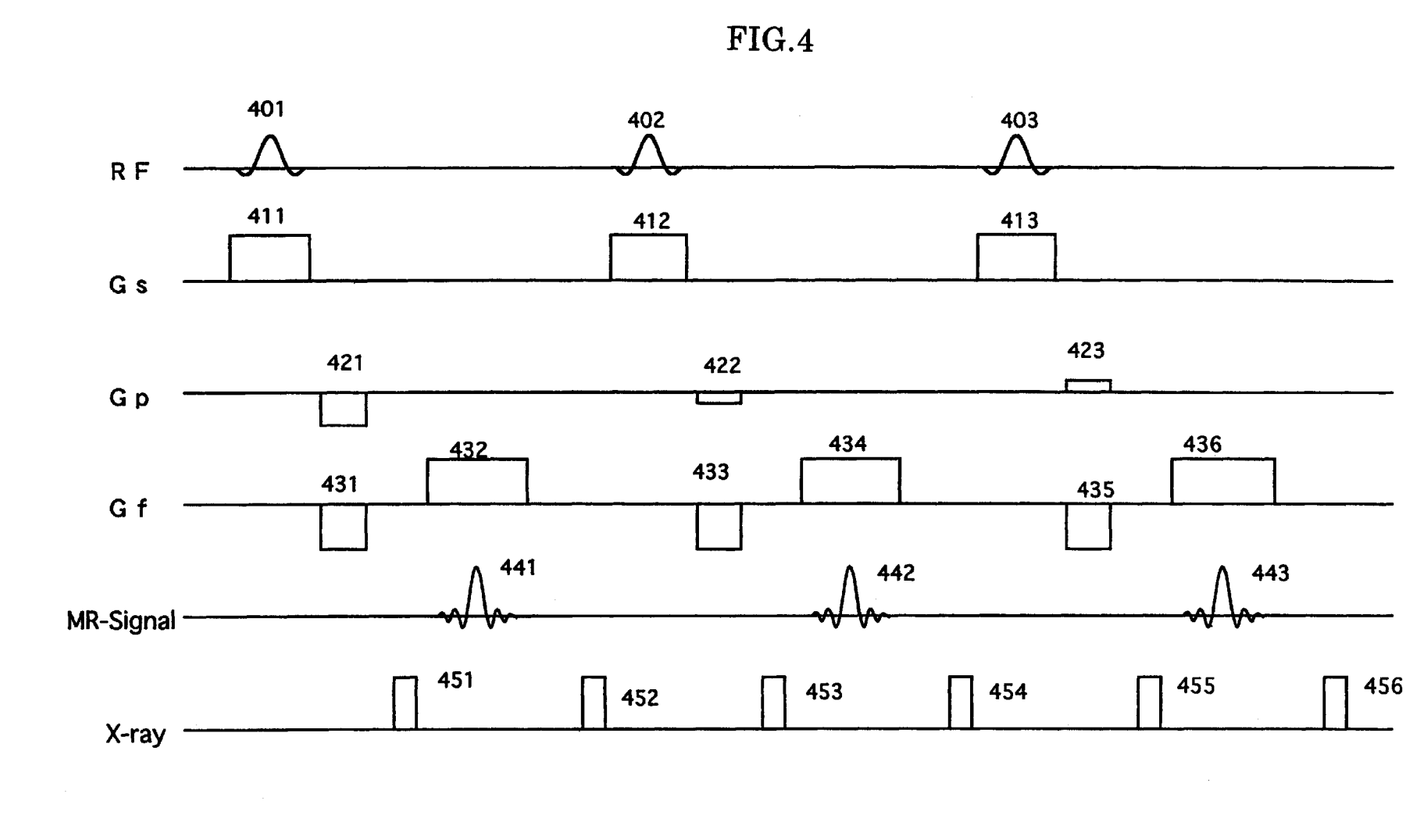
FIG. 4 is a timing chart showing a first embodiment of the medical imaging method according to the present invention.

An imaging method for the medical imaging apparatus having the above-mentioned constitution will be explained hereinafter. FIG. 4 shows a timing chart of a preferred embodiment of the imaging method according to the present invention, where the gradient echo method (GE method) is employed for the MRI sequence and X-ray fluoroscopy is carried out using pulse X-rays synchronously. In FIG. 4, timings of high frequency magnetic field pulses (RF pulses), gradient magnetic field pulses for slice selection (Gs pulses), gradient magnetic field pulses for phase encoding (Gp pulses), gradient magnetic field pulses for frequency encoding (Gf pulses), acquisition of echo signal in the MRI apparatus, and X-ray emission in the X-ray radiographic apparatus are presented from the top in this order.

The phase encoding gradient magnetic field is applied so that the intensity thereof varies every cycle of GE to obtain the position information and the cycle is repeated to obtain the required number of phase encoding steps for formation of a single image, e.g. 256.

According to this imaging method, in the MRI apparatus, an RF pulse 401 is applied together with a Gs pulse 411 at first and then a Gp pulse 421 and a Gf pulse 431 of negative polarity are applied. After a certain interval, a Gf pulse 432 having an opposite polarity to the Gf pulse 431 is applied and an echo signal 441 generated thereby is acquired. After a further interval, a Gs pulse 412 and an RF pulse 402 of the second cycle are applied and the same process is repeated except for the different intensity of the Gf pulse 422.

On the other hand, in the X-ray radiographic apparatus 10, the X-ray controller 17 drives the high voltage generator 16 using timing signals of Gf pulses (431, 433, 435 . . . ) and Gf pulses (432, 434, 436 . . . ) as triggers so that X-ray pulses 451, 452, 453 . . . are emitted.

In the GE method of this embodiment, the time duration for applying each RF pulse and each gradient magnetic field, the interval between the negative Gf pulse and the positive Gf pulse, the interval between acquisition of echo signal and application of the next RF pulse and the acquisition time of the echo signal are usually in the range of from several milliseconds to several tens of milliseconds respectively. In real time cine-radiography, the X-ray pulse emission time and the emission interval are usually in the range of from several milliseconds to several tens of milliseconds respectively.

Accordingly, the X-ray pulse 451 can be emitted between the negative Gf pulse 431 and the positive Gf pulse 432 and the X-ray pulse 452 within the interval from completion of acquisition of the echo signal 441 and application of the Gf pulse 432 to application of the next RF pulse 402. Similarly in the subsequent repetition cycles, the X-ray pulses are emitted intermittently within the intervals between the negative Gf pulses and the positive Gf pulses and in the time between cycle repetitions before the application of the next RF pulse to obtain continuous X-ray images (cine-images).

Thus, the times of application of each RF pulse and gradient magnetic field and the time of acquisition of each echo signal are controlled so as not to coincide with the time of X-ray emission, whereby X-ray images and MRI images both having almost the same time phase can be obtained while eliminating mutual electromagnetic interference between the apparatuses.

Although the X-ray pulse is emitted at the interval between the negative and positive Gf pulses and in the time between cycle repetition in the illustrated embodiment, the imaging method of the present invention is not limited to this. Various kinds of X-ray emission patterns can be realized by controlling the application timings of each of the above-mentioned pulses. For example, an interval may be inserted after the application of the RF pulse 401 and Gf pulse 411 before the application of the Gp pulse 421 and the Gf pulse 431 and the X-ray pulse may be emitted once within this interval. As a result, the X-ray pulse can be emitted three times within one cycle.

Figure 5:
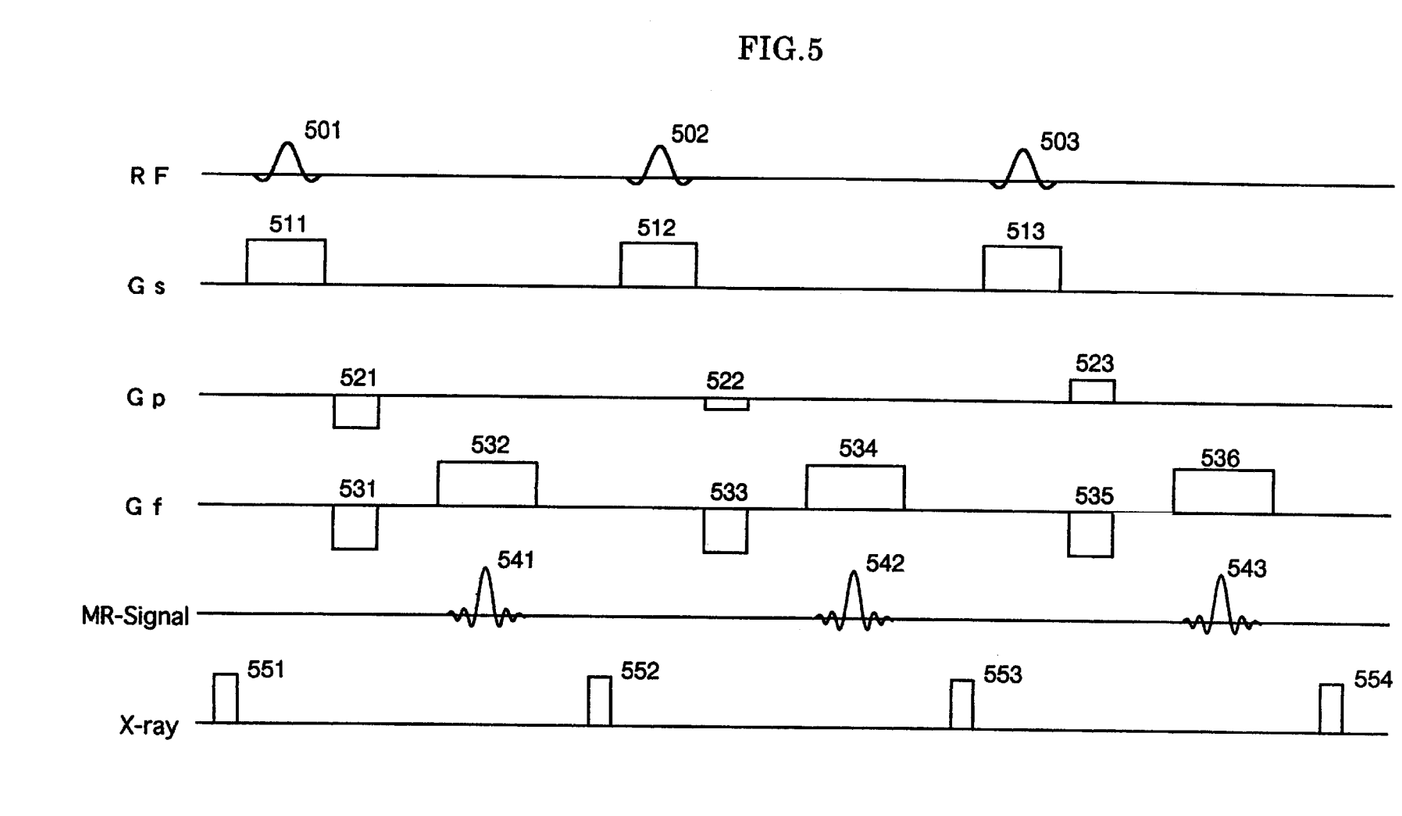
FIG. 5 is a timing chart showing a second embodiment of the medical imaging method according to the present invention.

Further, the X-ray pulse may be emitted once within a repetition of the pulse sequence of the MRI apparatus. For example, as shown in FIG. 5, X-ray pulses 551, 552 . . . may be emitted between the acquisition of the echo signal and the application of the next RF pulse.

Another embodiment of the imaging method for the medical imaging apparatus of the present invention will be explained with reference of FIG. 6.

In this embodiment, on the MRI apparatus side, pulse sequence 601, 602 . . . according to the EPI method are triggered by the timing signals of application of the X-ray pulses 611, 612 . . . . In the EPI sequence, Gf pulses are continuously and reversibly applied after a single shot of a RF pulse and an echo signal is collected at every reversion of the Gf pulse. The typical measuring time of one cycle of EPI is approximately several tens of milliseconds. Therefore, as shown in the example illustrated in FIG. 6, the X-ray pulse may be emitted once at the end of every cycle of the EPI sequence. As a result, the X-ray image and the MRI image are obtained alternatively and almost at the same time.

In this case, all of the echo signals required for formation of a single image may be collected after one shot of RF or the one-shot EPI sequence may be divided to several parts in order to shorten the interval of the X-ray emission. For example, if the echo signals for a single image are divided into three parts, three X-ray fluoroscopic images and one MRI image with approximately the same time phase can be obtained. Here, the X-rays having a pulse width of some 5 milliseconds may be emitted at relatively short intervals, e.g. 30 milliseconds, to obtain X-ray dynamic images with smooth motion.

Besides the EPI method, the other fast imaging methods where one cycle of pulse sequence is executed within several tens of milliseconds can be also applied to the imaging method of the present invention. As a fast imaging method, a spiral scanning method may be employed.

Figure 6:
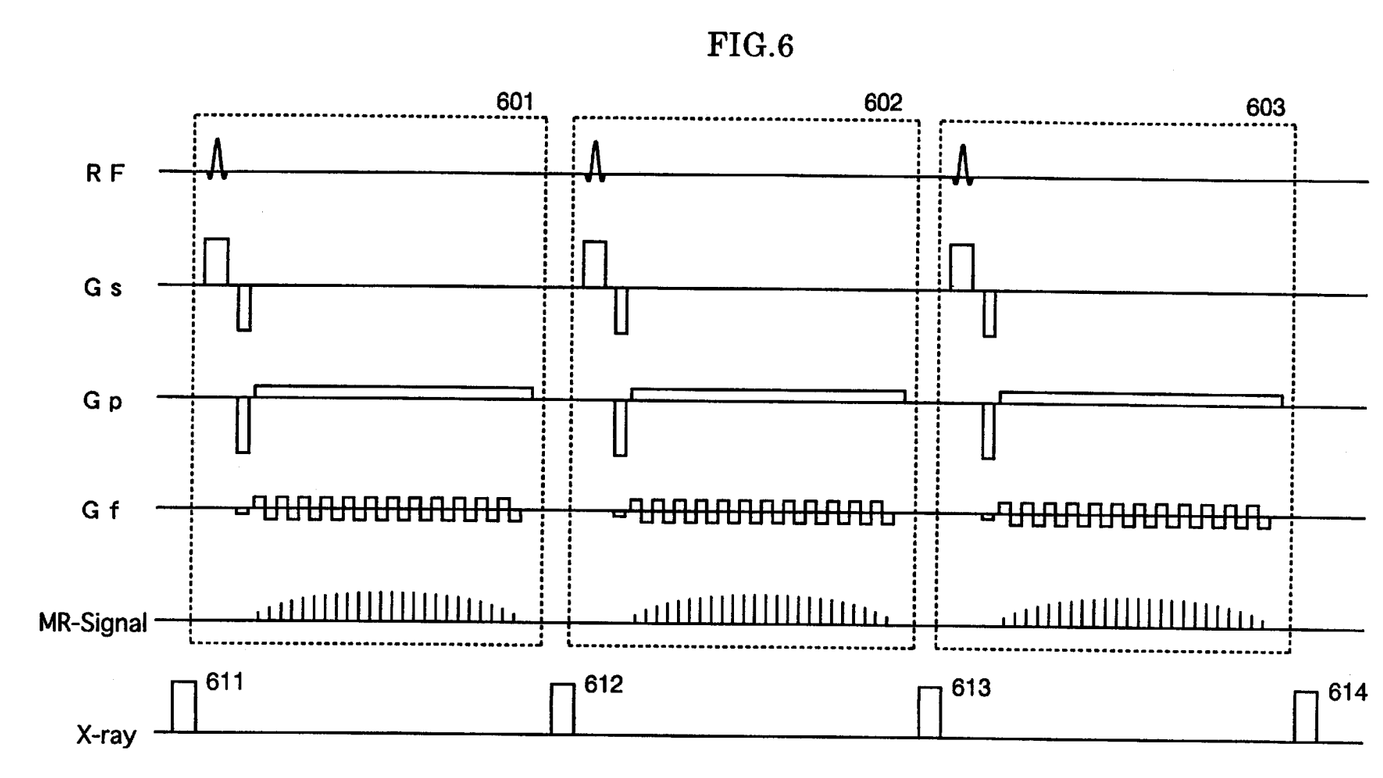
FIG. 6 is a timing chart showing a third embodiment of the medical imaging method according to the present invention.

Further, although the MRI images and the X-ray images are continuously obtained in the embodiment shown in FIG. 6, in case that a fast imaging method such as EPI is employed as the MRI method, MRI images may be obtained as occasion demands during the X-ray fluoroscopy. Such embodiment is shown in FIG. 7.

Figure 7:
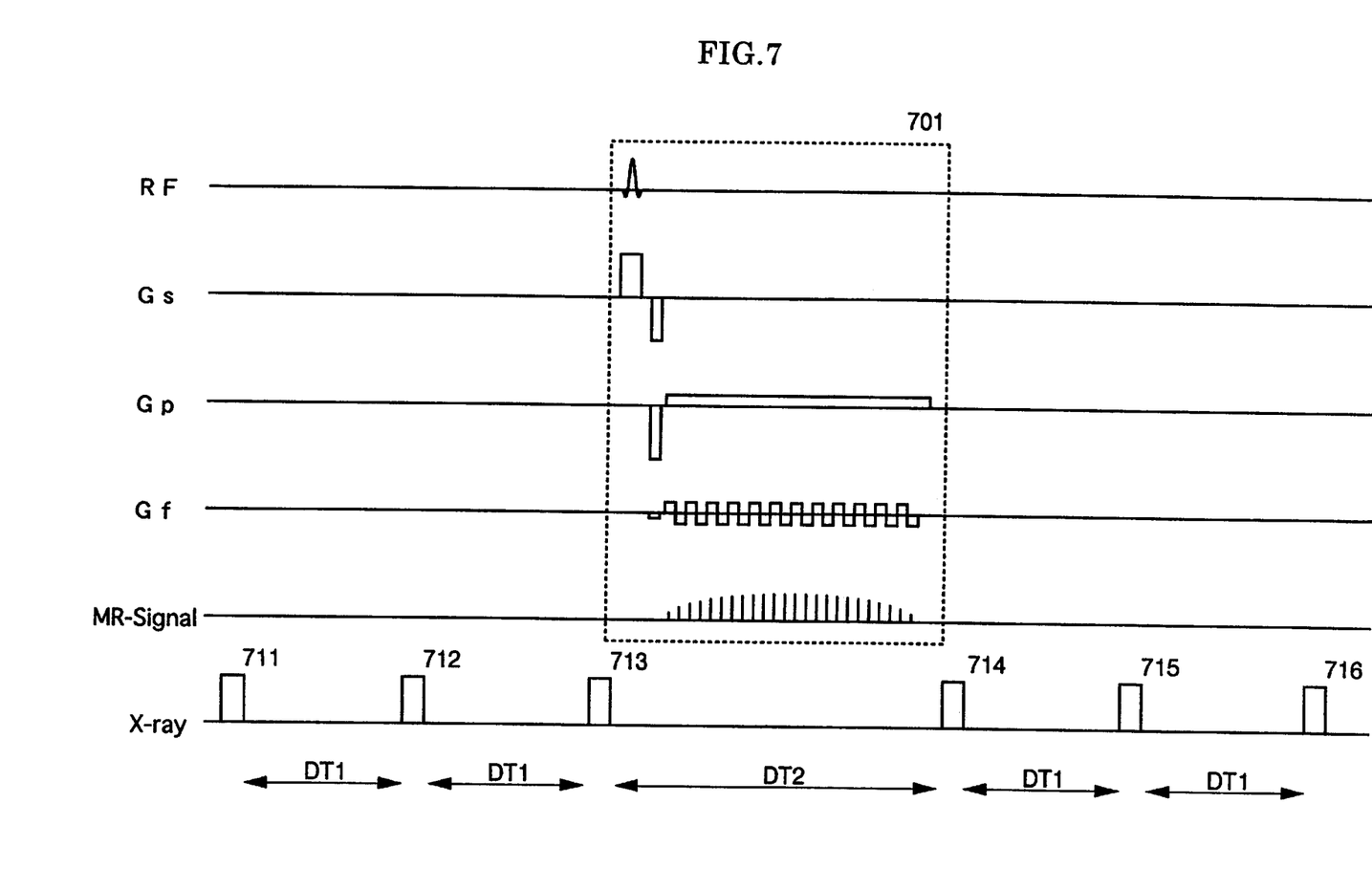
FIG. 7 is a timing chart showing a fourth embodiment of the medical imaging method according to the present invention.

In the method shown in FIG. 7, the MRI apparatus starts the pulse sequence according to EPI using timing signals for X-ray emission as triggers in the same manner as in the example shown in FIG. 6. However, the MRI sequence is executed only when it is required and otherwise X-ray radiography by X-ray emission with the predetermined timing is continued.

Unless MRI is conducted, the X-ray pulses 711, 712 . . . having a pulse width of some 5 milliseconds maybe emitted at a relatively short interval, e.g. 30 milliseconds, to obtain X-ray dynamic images with smooth motion. The interval time DT1 between pulses, for example 25 milliseconds, is shorter than the 40–50 milliseconds that is required for measurement of one image by the EPI method. Therefore, when the EPI sequence is performed, the interval between pulses is controlled to become longer than DT1. As illustrated in FIG. 7, three X-ray pulses 711–713 are emitted continuously at intervals of DT1. Then longer interval DT2, for example approximately 50 milliseconds, is set and a pulse sequence for one image by the EPI method is executed within this interval. Subsequently, the interval is restored to the shorter time DT1 to continue the X-ray emission 714–717.

The interval time DT2 is set as the time required for obtaining an MRI image and is approximately 50 milliseconds in the EPI sequence. Accordingly it can be kept short enough not to cause disturbance of the X-ray dynamic images. As a result, series of X-ray dynamic images and MRI images both having approximately the same time phase are obtained.

Though the exemplified imaging control means (image controller) 20 in the above-mentioned embodiment is connected to both the X-ray controller of the X-ray radiographic apparatus and the sequencer of the MRI apparatus, if either of them is a supervisory apparatus and controls the other, it may be connected to the supervisory apparatus and control it alone. In this case, the imaging control means can be installed inside the supervisory apparatus. Alternatively, separate imaging control means may be installed in the X-ray radiographic apparatus and the MRI apparatus or a controller of either apparatus may serve as the imaging control means.

As understood from the above explanation, X-ray images and MRI images both having approximately the same time phase can be obtained according to the present invention, while the X-ray images are not disturbed by the magnetic field generated by the MRI apparatus and the MRI images are not distorted by electromagnetic noise generated by the X-ray radiographic apparatus. It is not necessary to move the patient in order to take both of the images and safe, reliable and efficient therapy can be done in IVR where operation is performed while referring to both images.

In addition, according to the apparatus of the present invention, by employing a flat panel X-ray sensor, X-ray detecting efficiency is improved and the whole apparatus can be small sized because no hardware for magnetic shielding is required even though the MRI apparatus is used in combination.

Although the MRI means and X-ray radiographic means are operated at the same time in the above embodiments, they are not always operated simultaneously. For example, one of the MRI means and X-ray radiographic means is operated after measurement of the other. Or either is used independently. In this case also, space to be occupied by two apparatuses can be saved by use of a single apparatus of the present invention and it is not necessary to move an object to be examined between a plurality of measurement stations.

We claim:

1. A medical imaging apparatus comprising;

magnetic resonance imaging means for applying high frequency magnetic fields and gradient magnetic fields to an object placed in a static magnetic field according to a predetermined pulse sequence and obtaining a tomogram of the object based on nuclear magnetic resonance signals emitted from the object, X-ray radiographic means for obtaining a radiographic image of the object and, imaging control means connected to both the magnetic resonance imaging means and the X-ray radiographic means for controlling overall timings of application of magnetic fields and acquisition of the nuclear magnetic resonance signals in the magnetic resonance imaging means and timing of X-ray emission in the X-ray radiographic means.

2. The medical imaging apparatus of claim 1, wherein the image control means controls the timing of X-ray emission to be noncoincident with both the timing of application of magnetic fields and the timing of acquisition of NMR signals.

3. The medical imaging apparatus of claim 1, wherein the X-ray radiographic means has an X-ray generator and an X-ray detector and the X-ray detector is a flat panel X-ray sensor.

4. The medical imaging apparatus of claim 2, wherein the image control means controls the timing of X-ray emission so that X-ray is emitted before and after acquisition of an NMR signal(s).

5. The medical imaging apparatus of claim 2, wherein the image control means controls the timing of X-ray emission so that X-ray is emitted between acquisition of an NMR signal and application of a high frequency magnetic field.

6. The medical imaging apparatus of claim 1, wherein the pulse sequence is a sequence according to an echo planar imaging method and the image control means controls the timing of X-ray emission so that the pulse sequence is carried out within intervals between X-ray pulses.

7. The medical imaging apparatus of claim 6, wherein an interval between the X-ray pulses is controlled to be longer when the pulse sequence is carried out within the interval.

8. The medical imaging apparatus of claim 1, wherein the image control means controls the timing of X-ray emission to obtain X-ray fluoroscopic images when measurement of the magnetic resonance imaging means is not carried out.

9. The medical imaging apparatus of claim 1, wherein the image control means controls the timing of application of magnetic fields and acquisition of the nuclear magnetic resonance signals in the magnetic resonance imaging means when X-ray radiography is not carried out.

10. The medical imaging apparatus of claim 1, wherein the MRI means is provided with detecting means, the detecting means being placed near the object to be examined so that X-ray image thereof does not overlap an X-ray image of a portion of interest of the object.

11. A method for producing X-ray radiographic images and MRI images approximately at the same time, the method comprising the steps of:

applying high frequency magnetic fields and gradient magnetic fields to an object to be examined in a static magnetic field according to a predetermined pulse sequence to obtain tomograms of the object based on nuclear magnetic resonance signals emitted from the object, emitting X-rays onto the object to obtain radiographic images of the object, the X-ray emissions being conducted in parallel with the application of the high frequency magnetic fields and the gradient magnetic fields, and, controlling timings of application of magnetic fields and acquisition of NMR signals and timing of X-ray emission so that the timing of X-ray emissions is noncoincident with both the timing of application of magnetic fields and the timing of acquisition of NMR signals.

12. The method of claim 11, wherein the X-rays are emitted as pulses.

13. The method of claim 12, wherein the pulse sequence is a sequence according to an echo planar imaging method and the sequence is carried out within intervals between the X-ray pulses emitted intermittently.

14. The method of claim 12, wherein the X-rays are emitted within intervals between magnetic field pulses constituting the pulse sequence.

15. A medical imaging apparatus comprising:

a pair of static magnetic field generating means arranged in mutual opposition with an object between them, for generating static magnetic field to produce a homogeneous magnetic field area;

gradient magnetic field generating means for generating a gradient magnetic field in the homogeneous magnetic field area;

high frequency magnetic field generating means for generating a high frequency magnetic field;

an X-ray source for irradiating the object with X-rays so that at least a part of the irradiated area overlaps the homogeneous magnetic field area;

an X-ray detector, disposed in opposition to the X-ray source with the object between them, for detecting X-rays transmitted through the object; and an image controlling means for controlling the timing of the gradient magnetic field generation, the timing of the high frequency magnetic field generation and the timing of the X-ray emission.

16. The medical imaging apparatus of claim 15, wherein the X-ray source and the X-ray detector are arranged in the direction perpendicular to the direction of the static magnetic field.

17. The medical imaging apparatus of claim 15, wherein the X-ray source and the X-ray detector are arranged in the direction parallel with the direction of the static magnetic field.

18. A medical imaging apparatus comprising:

static magnetic field generating means for generating static magnetic field to produce a homogeneous magnetic field area around an object;

gradient magnetic field generating means for generating gradient magnetic fields in the homogeneous magnetic field area;

high frequency magnetic field generating means for generating high frequency magnetic field;

a gantry accommodating the static magnetic field generating means, the gradient magnetic field generating means and the high frequency magnetic field generating means, and defining a space wherein the object is placed, an X-ray source arranged at the gantry for irradiating the object with X-rays, and an X-ray detector placed opposite to the X-ray source with regard to the object for detecting X-rays transmitted through the object.

19. The medical imaging apparatus of claim 18, wherein the X-ray source emits X-rays so that at least a part of the irradiated area overlaps with the homogeneous magnetic field area.

20. The medical imaging apparatus of claim 18, wherein the X-ray source and the X-ray detector are placed on the surface of the gantry.

21. The medical imaging apparatus of claim 18, wherein the X-ray source and the X-ray detector are accommodated in the gantry.

22. The medical imaging apparatus of claim 18, wherein the apparatus having a pair of gantries arranged in mutual opposition with the object between them and each of the pair accommodates the static magnetic field generating means, the gradient magnetic field generating means, and the high frequency magnetic field generating means.

23. The medical imaging apparatus of claim 22, wherein the X-ray source and the X-ray detector are placed on the surface of one of the gantries.

24. The medical imaging apparatus of claim 22, wherein one of the gantries is equipped with the X-ray source and another is equipped with the X-ray detector.

* * * * *